US008318989B2

(12) United States Patent
Kourtakis et al.

(10) Patent No.: US 8,318,989 B2
(45) Date of Patent: *Nov. 27, 2012

(54) PROCESS FOR PRODUCING GUERBET ALCOHOLS USING WATER TOLERANT BASIC CATALYSTS

(75) Inventors: Kostantinos Kourtakis, Media, PA (US); Ronnie Ozer, Arden (DE); Michael B. D'Amore, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 410 days.

This patent is subject to a terminal disclaimer.

(21) Appl. No.: 12/642,954

(22) Filed: Dec. 21, 2009

(65) Prior Publication Data

US 2010/0160693 A1 Jun. 24, 2010

Related U.S. Application Data

(60) Provisional application No. 61/139,915, filed on Dec. 22, 2008, provisional application No. 61/139,931, filed on Dec. 22, 2008.

(51) Int. Cl.
*C07C 27/08* (2006.01)
(52) U.S. Cl. .................................. 568/902.2; 568/905
(58) Field of Classification Search ............... 568/902.2, 568/905
See application file for complete search history.

(56) References Cited

U.S. PATENT DOCUMENTS

| | | | |
|---|---|---|---|
| 2,457,866 A | 1/1949 | Carter | |
| 5,300,695 A | 4/1994 | Radlowski | |
| 2007/0255079 A1 | 11/2007 | Tsuchida et al. | |
| 2009/0054672 A1 | 2/2009 | Kourtakis | |
| 2009/0054703 A1 | 2/2009 | Kourtakis | |
| 2009/0054704 A1 | 2/2009 | Kourtakis | |
| 2009/0054705 A1 | 2/2009 | Kourtakis | |
| 2009/0054706 A1 | 2/2009 | Kourtakis | |
| 2009/0054707 A1 | 2/2009 | Kourtakis | |

FOREIGN PATENT DOCUMENTS

| | | |
|---|---|---|
| JP | WO2006/059729 A1 | 8/2006 |
| WO | WO/2009/097310 | 6/2009 |
| WO | WO/2009/097312 | 6/2009 |

OTHER PUBLICATIONS

J. Logsdon, "Kirk-Othmer Encyclopedia of Chemical Technology," John Wiley and Sons, inc., NY (2001) (Book—Not Available).
Michael N. Dvornikoff et al., "J. of Organic Chemistry," Condensation of Alcohols, vol. 22, pp. 540-542 (1956) [Contribution from St Louis Research Dept., Organic Chemicals Div., Monsanto Chemical Co.].
J. I. DiCosimo et al., "J. of Catalysis," Structure and Surface and Catalytic Properties of Mg-Al Basic Oxides, vol. 178, pp. 499-510 (1998).
A. Cuneyt Tas, "J. of the European Ceramic Society," Combustion synthesis of calcium phosphate bioceramic powders, vol. 20, pp. 2389-2394 (2000).
J. I. DiCosimo et al., "J. of Catalysis," Structural Requirements and Reaction Pathways in Condensation Reactions of Alcohols on MgyALOx Catalysts, vol. 190, pp. 261-275 (2000).
N. N. Das et al., "Bull Mater Sci.," Catalytic characterization of bi-functional catalysts derived from Pd-Mg-Al layered double hydroxides, vol. 25, No. 4, pp. 283-289 (Aug. 2002).
V. K. Diez et al., "Latin American Applied Research," Effect of the Acid-Based Properties of Mg-Al Mixed Oxides on the Catalyst Deactivation During Aldol Condensation Reactions, vol. 33, pp. 79-86 (2003).
Carlo Carlini at al., "J. of Molecular Catalysis A: Chemical," Guerbet condensation of methanol with n-propanol to isobutyl alcohol over heterogeneous copper chromite/Mg-A1 mixed oxides catalysts, vol. 220, pp. 215-220 (2004).
Carlo Carlini et al., "J. of Molecular Catalysts A: Chemical," Guerbet condensation of methanol with n-propanol to isobutyl alcohol over heterogeneous bifunctional catalysts based on Mg-A1 mixed oxides partially substituted by different metal components, vol., 232, pp. 13-20, (2005).

*Primary Examiner* — Sikarl Witherspoon
(74) *Attorney, Agent, or Firm* — Kevin S. Dobson (57) ABSTRACT

A process is provided for making a reaction product comprising 1-butanol by contacting a reactant comprising ethanol containing a significant amount of water with a decomposed hydrotalcite catalyst. The catalyst may be 1) hydrotalcites which have been thermally decomposed, either partially or fully, to form catalytically active species; 2) combinations of hydrotalcites (optionally containing transition metals) and metal carbonates; and 3) hydrotalcites (optionally containing transition metals) surface-impregnated with a transition metal nitrate, where catalysts 2) and 3) have also been thermally decomposed, either partially or fully, to form catalytically active species. The catalyst, at a selected reaction time, has greater activity when the ethanol contains water as compared to when the ethanol is anhydrous.

17 Claims, 4 Drawing Sheets

PROCESS FOR PRODUCING GUERBET ALCOHOLS USING WATER TOLERANT BASIC CATALYSTS

CROSS-REFERENCE TO RELATED APPLICATIONS

This application claims benefit of priority from Provisional Application No. 61/139,915 filed Dec. 22, 2008, and from Provisional Application No. 61/139,931 filed Dec. 22, 2008. This application hereby incorporates by reference Provisional Application Nos. 61/139,915 and 61/139,931 in their entirety.

FIELD OF THE INVENTION

The present invention relates to a process for the catalytic conversion of ethanol containing water to a reaction product comprising 1-butanol using three types of catalysts. The catalysts may be 1) hydrotalcites which have been thermally decomposed, either partially or fully, to form catalytically active species; 2) combinations of hydrotalcites (optionally containing transition metals) and metal carbonates; and 3) hydrotalcites (optionally containing transition metals) surface-impregnated with a transition metal nitrate, where catalysts 2) and 3) have also been thermally decomposed, either partially or fully, to form catalytically active species. The use of ethanol containing a significant amount of water provides an improved relative conversion at an extended reaction time compared to the use of anhydrous ethanol.

BACKGROUND

Efforts directed at improving air quality and increasing energy production from renewable resources have resulted in renewed interest in alternative fuels, such as ethanol and butanol, that might replace gasoline and diesel fuel, or be used as additives in gasoline and diesel fuel.

Methods for producing 1-butanol from ethanol are known. For example, 1-butanol can be prepared by condensation from ethanol over basic catalysts at high temperature using the so-called "Guerbet Reaction" (see for example, J. Logsdon in Kirk-Othmer Encyclopedia of Chemical Technology, John Wiley and Sons, Inc., New York, 2001). Methods of using catalysts to convert ethanol to butanol are also discussed in the following references.

M. N. Dvornikoff and M. W. Farrar, J. of Organic Chemistry (1957), 11, 540-542, disclose the use of MgO—$K_2CO_3$—$CuCrO_2$ catalyst system to promote ethanol condensation to higher alcohols, including 1-butanol. The disclosed liquid phase reaction using this catalyst showed a 13% conversion of ethanol and 47% selectivity to 1-butanol.

U.S. Pat. No. 5,300,695, assigned to Amoco Corp., discloses processes in which an alcohol having X carbon atoms is reacted over an L-type zeolite catalyst to produce a higher molecular weight alcohol. In some embodiments, a first alcohol having X carbon atoms is condensed with a second alcohol having Y carbon atoms to produce an alcohol having X+Y carbons. In one specific embodiment, ethanol is used to produce butanol using a potassium L-type zeolite.

J. I. DiCosimo, et al., in Journal of Catalysis (2000), 190 (2), 261-275, describe the effect of composition and surface properties on alcohol-coupling reactions using $Mg_yAlO_x$ catalysts for alcohol reactions, including ethanol. Also condensation reactions on $Mg_yAlO_x$ samples involved the formation of products containing a new C—C bond, such as n-$C_4H_8O$ (or n-$C_4H_9OH$) and iso-$C_4H_8O$ (or iso-$C_4H_9OH$).

They also describe, in Journal of Catalysis (1998), 178(2), 499-510, that the oxidation to acetaldehyde and the aldol condensation to n-butanol both involve initial surface ethoxide formation on a Lewis acid-strong base pair.

Carlini et al. describe a catalytic reaction of methanol with n-propanol to produce isobutyl alcohol. The involved catalyst is a calcined hydrotalcite in combination with copper chromite. See C. Carlini et al, Journal of Molecular Catalysis A: Chemical (2005), 232 (1-2) 13-20. See also C. Carlini, Journal of Molecular Catalysis A: Chemical (2004), 220 (2), 215-220, in which the catalyst is a mixture of a hydrotalcite with Pd, Ni, Rh, or Cu, with the mixture being calcined at 500° C.

In the production of Guerbet alcohols, drying of the ethanol feedstock is typically necessary to avoid inhibition or deactivation of the catalyst. The present invention provides a process for converting an ethanol feed containing significant amounts of water into a reaction product comprising 1-butanol using catalysts derived from hydrotalcite precursors. Surprisingly, the use of an ethanol feed which contains significant amounts of water does not diminish the activity of the catalysts with extended use.

SUMMARY OF THE INVENTION

The present invention provides processes for converting an ethanol feed containing significant amounts of water into a reaction product comprising 1-butanol using certain catalysts derived from hydrotalcite precursors. In one embodiment of the invention, a process is provided, the process comprising: contacting a reactant comprising ethanol containing water with a catalyst at a reaction temperature and pressure sufficient to produce said reaction product, wherein said catalyst is derived from a hydrotalcite of Formula I:

Formula I wherein
$M^{2+}$ is divalent Mg, or a combination of divalent Mg and at least one divalent member selected from the group consisting of Zn, Ni, Pd, Pt, Co, Fe, and Cu;
$M^{3+}$ is trivalent Al, or a combination of trivalent Al and at least one trivalent member selected from the group consisting of Fe and Cr;
x is 0.66 to 0.1;
M' is one or more divalent members selected from the group consisting of Ni and Co;
A' is the anion of ethylenediaminetetraacetic acid;
n' is the absolute value of the sum of the oxidation state of M' and the oxidation state of the anion of ethylenediaminetetraacetic acid (−4);
$A^{n-}$ is $CO_3^{2-}$ with n=2 or $OH^-$ with n=1;
a=0.001 to 1; and
y=0 to 4;
wherein the hydrotalcite catalyst is partially decomposed; and wherein the Wet:Dry Activity Ratio obtained by the Relative Conversion Test is greater than 100% after 70 minutes of time on stream.

Referring to Formula I, in some embodiments, $M^{2+}$ is divalent Mg. In some embodiments, $M^{3+}$ is trivalent Al. In some embodiments, $A^{n-}$ is $CO_3^{2-}$ or $OH^-$. In some embodiments, $M^{2+}$ is divalent Mg; $M^{3+}$ is trivalent Al; x is 0.2; a is 0.1; A' is the anion of ethylenediaminetetraacetic acid; M' is Ni; $A^{n-}$ is $OH^-$; n' is 2; n is 1; and y is 0 to 4.

In one embodiment of the invention, a process is provided, the process comprising: contacting a reactant comprising ethanol containing water with a catalyst at a reaction temperature and pressure sufficient to produce said product, wherein said catalyst is derived from a hydrotalcite of Formula II:

Formula II wherein $M^{2+}$ is divalent Mg and at least one divalent member selected from the group consisting of Ni and Co;

$M^{3+}$ is trivalent Al, or a combination of trivalent Al and at least one trivalent member selected from the group consisting of Fe and Cr;

x is 0.66 to 0.1;

$A^{n-}$ is $CO_3^{2-}$ with n=2 or $OH^-$ with n=1; and y is 0 to 4;

wherein the hydrotalcite catalyst is partially decomposed; and wherein the Wet:Dry Activity Ratio obtained by the Relative Conversion Test is greater than 100% after 70 minutes of time on stream.

Referring to Formula II, in some embodiments, $M^{2+}$ is divalent Mg. In some embodiments, $M^{3+}$ is trivalent Al. In some embodiments, $A^{n-}$ is $CO_3^{2-}$ or $OH^-$. In some embodiments, $M^{2+}$ is divalent Mg and at least one divalent member selected from the group consisting of Ni and Co; $M^{3+}$ is trivalent Al: and $A^{n-}$ is $CO_3^{2-}$ or $OH^-$. In some embodiments, $M^{2+}$ is divalent Mg and at least one divalent member selected from the group consisting of Ni and Co, and x is 0.35 to 0.1.

In one embodiment of the invention, a process is provided, the process comprising: contacting a reactant comprising ethanol containing water with a catalyst at a reaction temperature and pressure sufficient to produce the reaction product, wherein the catalyst is derived from a hydrotalcite of Formula III:

Formula III wherein $M^{2+}$ is divalent Mg, or a combination of Mg and at least one divalent member selected from the group consisting of Zn, Ni, Pd, Pt, Co, Fe, and Cu;

$M^{3+}$ is trivalent Al, or a combination of trivalent Al and at least one trivalent member selected from the group consisting of Fe and Cr;

x is 0.66 to 0.1;

$A^{n-}$ is $CO_3^{2-}$ with n=2, or $OH^-$ with n=1;

M'A' is a carbonate of at least one divalent metal M' selected from the group consisting of Ni and Co; and A' is carbonate;

z is any number between 0.001 and 0.5 inclusive; and y is 0 to 4;

wherein the hydrotalcite catalyst is partially decomposed; and wherein the Wet:Dry Activity Ratio obtained by the Relative Conversion Test is greater than 100% after 70 minutes of time on stream.

Referring to Formula III, in some embodiments, $M^{2+}$ is divalent Mg. In some embodiments, $M^{3+}$ is trivalent Al. In some embodiments, $A^{n-}$ is $CO_3^{2-}$ or $OH^-$. In some embodiments, $M^{2+}$ is divalent Mg; $M^{3+}$ is trivalent Al; $A^{n-}$ is $CO_3^{2-}$ or OH; z is any number between 0.001 and 0.5; and M' is selected from the group consisting of Ni and Co. In some embodiments, z is any number between 0.01 and 0.25.

In another embodiment of the invention, a process is provided, the process comprising: contacting a reactant comprising ethanol containing water with a catalyst at a reaction temperature and pressure sufficient to produce the reaction product, wherein the catalyst is derived from a hydrotalcite of Formula IV:

Formula IV wherein $M^{2+}$ is divalent Mg, or a combination of Mg and at least one divalent member selected from the group consisting of Zn, Ni, Pd, Pt, Co, Fe, and Cu;

$M^{3+}$ is trivalent Al, or a combination of trivalent Al and at least one trivalent member selected from the group consisting of Fe and Cr;

x is 0.66 to 0.1;

$A^{n-}$ is $CO_3^{2-}$ with n=2, or $OH^-$ with n=1;

$M'(A')_2$ is a nitrate or hydroxide of at least one divalent metal M' selected from the group consisting of Ni and Co; and A' is nitrate or hydroxide;

z is any number between 0.001 and 0.5 inclusive;

y is 0 to 4;

wherein the hydrotalcite catalyst is partially decomposed; and wherein the Wet:Dry Activity Ratio obtained by the Relative Conversion Test is greater than 100% after 70 minutes of time on stream.

Referring to Formula IV, in some embodiments, $M^{2+}$ is divalent Mg. In some embodiments, $M^{3+}$ is trivalent Al. In some embodiments, $A^{n-}$ is $CO_3^{2-}$ or $OH^-$. In some embodiments, $M^{2+}$ is divalent Mg; $M^{3+}$ is trivalent Al; x=0.25; $A^{n-}$ is $CO_3^{2-}$; M' is Ni; A' is nitrate; and z=0.06; and y is 0 to 4. In some embodiments, A' is nitrate; z is any number between 0.01 and 0.2; $A^{n-}$ is $CO_3^{2-}$; and n=2.

According to the processes of the invention, the hydrotalcite decomposition may be achieved by heating the hydrotalcite for a time and at a temperature sufficient to cause a diminution in the hydrotalcite powder X-ray diffraction pattern peak intensities between 2θ angles of 10 degrees and 70 degrees using CuKα radiation.

According to the processes of the invention, the ethanol contains about 0.5 weight percent to about 20 weight percent water. In some embodiments, the ethanol contains about 2 weight percent to about 8 weight percent water. The reaction temperature is from about 200° C. to about 500° C. and the pressure is from about 0.1 MPa to about 20.7 MPa.

In some embodiments, the Wet:Dry Activity Ratio is greater than 100% after 90 minutes of time on stream. In some embodiments, the Wet:Dry Activity Ratio is greater than 100% after 180 minutes of time on stream. In some embodiments, the Wet:Dry Activity Ratio is greater than 100% after 300 minutes of time on stream.

DETAILED DESCRIPTION

The present invention relates to a catalytic process for making a reaction product comprising 1-butanol from wet ethanol. Useful applications for the 1-butanol, which can be separated from the reaction product, include as an additive or blend component to diesel fuel. Ethanol is produced from renewable resources such as corn, sugar cane, or cellulosic feeds. In countries where ethanol production is operated at large scale such as Brazil, the ability to produce 1-butanol from ethanol offers an advantage.

It is widely known that ethanol can be recovered from a number of sources, including synthetic and fermentation feedstocks. Ethanol derived from fermentation processes typically contains water. Removal of this water is relatively facile up to the ethanol/water azeotrope (96.4% ethanol/3.6% water at atmospheric pressure). Further drying of the ethanol can be accomplished using molecular sieves and is typically necessary to avoid inhibition or deactivation of downstream catalyst. However, the capital investment and operational costs associated with this additional drying step can make the economics of butanol production from ethanol less attractive. The ability to use ethanol containing a significant amount of water, for example the amount of water corresponding to an ethanol/water azeotrope where the water is present at greater than about 0.5 weight percent, and a catalyst that is tolerant to that much water, would provide an economic advantage for a process to make 1-butanol, as in a Guerbet alcohol synthesis.

The following definitions are used herein and should be referred to for interpretation of the claims and the specification.

The term "hydrotalcites" refers to layered, double hydroxides of the general formula $(M^{2+}_{1-x}M^{3+}_x(OH)_2)(A^{n-}_{x/n}) \cdot yH_2O$ The $M^{2+}$ ions can be a variety of divalent cations (e.g., Mg, Ni, Pt, Pd, Zn, Co, Fe, Cu) and the $M^{3+}$ ions can be trivalent Al, Fe or Cr. Some hydrotalcites are described by V. K. Diez, C. R. Apesteguia, and J. I. DiCosimo (*Latin American Applied Research*, 33, 79-86 (2003)) and N. N. Das and S. C. Srivastava (*Bull. Mater. Sci.* 25, (4), 283-289 (2002)).

The term "anhydrous ethanol" means ethanol containing less than about 0.1 weight percent water. As used herein, the term "dry ethanol" is used interchangeably with anhydrous ethanol.

The term "significant amount of water", as used herein, means more than a trace amount of water, and refers to ethanol which contains about 0.5 weight percent to about 20 weight percent water, for example about 2 weight percent to about 8 weight percent water.

The term "ethanol conversion" means the chemical reaction of ethanol to another compound.

The term "unreacted ethanol" means ethanol which has not been chemically reacted to another compound.

The term "time on stream" means reaction time measured from the time when the reaction product comprising 1-butanol first exits the reactor. As used herein, "time on stream" is used interchangeably with "elapsed time."

The terms "Guerbet alcohol products" or "Guerbet alcohols" mean one or more alcohols produced by the Guerbet synthesis, wherein a primary or secondary alcohol having a methylene group at the α-position is condensed with itself, or with another alcohol also having a methylene group, to form a higher alcohol containing twice the number of carbon atoms of the single starting alcohol or, in the case of mixed alcohols, the sum of the number of carbon atoms in each reacting pair of alcohols. 1-Butanol is a Guerbet alcohol product of ethanol.

The term "base catalyst" means either a substance which has the ability to accept protons as defined by Brönsted, or a substance which has an unshared electron pair with which it can form a covalent bond with an atom, molecule or ion as defined by Lewis.

The term "wt %" means weight percent.
The term, "° C." means degrees Celsius.
The term "mg" means milligram.
The term "min" means minutes.
The term "mL" means milliliter.
The term "M" means molar.
The term "o.d." means outer diameter.
The term "cc" means cubic centimeter.
The term "cm" means centimeter.
The term "temp" means temperature.
The term "MPa" means mega Pascal.
The term "GC/MS" means gas chromatography/mass spectrometry.

GENERAL METHODS AND MATERIALS

The catalysts useful in the present invention are 1) hydrotalcites which have been thermally decomposed, either partially or fully, to form catalytically active species; 2) combinations of hydrotalcites (optionally containing transition metals) and metal carbonates; and 3) hydrotalcites (optionally containing transition metals) surface-impregnated with a transition metal nitrate, where catalysts 2) and 3) have also been thermally decomposed, either partially or fully, to form catalytically active species.

In one embodiment, the catalysts are partially or fully thermally decomposed hydrotalcites having, prior to thermal decomposition, the empirical formula below:

$[M^{2+}_{1-x}M^{3+}_x(OH)_2][\{(M'A')^{n'-}\}_a A^{n-}_{(1-a)(n'/n)}]_{x/n'} \cdot y H_2O$     Formula I wherein
$M^{2+}$ is divalent Mg, or a combination of divalent Mg and at least one divalent member selected from the group consisting of Zn, Ni, Pd, Pt, Co, Fe, and Cu;
$M^{3+}$ is trivalent Al, or a combination of trivalent Al and at least one trivalent member selected from the group consisting of Fe and Cr;
x is 0.66 to 0.1;
M' is one or more divalent members selected from the group consisting of Ni and Co;
A' is the anion of ethylenediaminetetraacetic acid;
n' is the absolute value of the sum of the oxidation state of M' (i.e., +2) and the oxidation state of the anion of ethylenediaminetetraacetic acid (−4) (for example, for M'A' wherein M' is $Ni^{2+}$ with an oxidation state of +2, n' is 2);
$A^{n-}$ is $CO_3^{2-}$ with n=2 or $OH^-$ with n=1;
a=0.001 to 1; and
y=0 to 4.

In a preferred embodiment, $M^{2+}$ is divalent Mg; $M^{3+}$ is trivalent Al; $A^{n-}$ is $CO_3^{2-}$ or $OH^-$; and a is 0.1 to 0.44.

In another embodiment, the catalysts are partially or fully thermally decomposed hydrotalcites having the empirical formula below:

$(M^{2+}_{1-x}M^{3+}_x(OH)_2)(A^{n-}_{x/n}) \cdot yH_2O$     Formula II wherein
$M^{2+}$ is divalent Mg and at least one divalent member selected from the group consisting of Ni and Co;
$M^{3+}$ is trivalent Al, or a combination of trivalent Al and at least one trivalent member selected from the group consisting of Fe and Cr;
x is 0.66 to 0.1; and
$A^{n-}$ is $CO_3^{2-}$ with n=2, or $OH^-$ with n=1; and
y is 0 to 4.

In a preferred embodiment, $M^{2+}$ is divalent Mg and at least one divalent member selected from the group consisting of Ni and Co, and x is 0.35 to 0.1.

In one embodiment, the catalysts are partially or fully thermally decomposed hydrotalcite/metal carbonate combinations of a hydrotalcite of the formula $[(M^{2+}_{1-x}M^{3+}_x(OH)_2)(A^{n-}_{x/n})].yH_2O]$ and a metal carbonate of the formula [M'A']. The combinations, prior to thermal decomposition, have the empirical formula below $$[[(Me^{2+}_{1-x}M^{3+}_x(OH)_2)(A^{n-}_{x/n})].yH_2O][M'A']_z \quad \text{Formula III}$$

wherein
$M^{2+}$ is divalent Mg, or a combination of Mg and at least one divalent member selected from the group consisting of Zn, Ni, Pd, Pt, Co, Fe, and Cu;
$M^{3+}$ is trivalent Al, or a combination of trivalent Al and at least one trivalent member selected from the group consisting of Fe and Cr;
x is 0.66 to 0.1;
$A^{n-}$ is $CO_3^{2-}$ with n=2, or $OH^-$ with n=1;
M'A' is a carbonate of at least one divalent metal M' selected from the group consisting of Ni and Co; and A' is carbonate;
z is any number in the range of 0.001 to 0.5, inclusive (i.e., including the endpoints of the range); and
y is 0 to 4.

In a preferred embodiment, $M^{2+}$ is divalent Mg; $M^{3+}$ is trivalent Al; $A^{n-}$ is $CO_3^{2-}$ or $OH^-$; z is any number between 0.001 and 0.5; and M' is selected from the group consisting of Ni and Co. Preferred values for z are in the range between 0.01 and 0.25, including the endpoints of the range.

In another embodiment, the catalysts are partially or fully thermally decomposed hydrotalcites which are surface-impregnated with a transition metal nitrate containing nickel or cobalt before decomposition. Prior to thermal decomposition, these hydrotalcites have the empirical formula below:

$$[[(M^{2+}_{1-x}M^{3+}_x(OH)_2)(A^{n-}_{x/n})].yH_2O][M'(A')_2]_z \quad \text{Formula IV}$$

wherein
$M^{2+}$ is divalent Mg, or a combination of Mg and at least one divalent member selected from the group consisting of Zn, Ni, Pd, Pt, Co, Fe, and Cu;
$M^{3+}$ is trivalent Al, or a combination of trivalent Al and at least one trivalent member selected from the group consisting of Fe and Cr;
x is 0.66 to 0.1; and
$A^{n-}$ is $CO_3^{2-}$ with n=2, or $OH^-$ with n=1;
$M'(A')_2$ is a nitrate or hydroxide of at least one divalent metal M' selected from the group consisting of Ni and Co; and A' is nitrate or hydroxide;
z is any number between 0.001 and 0.5 inclusive; and
y is 0 to 4.

In a preferred embodiment, $M^{2+}$ is divalent Mg; $M^{3+}$ is trivalent Al; x=0.25; $A^{n-}$ is $CO_3^{2-}$; M' is Ni; A' is nitrate; and z=0.06; and y is 0 to 4.

In a preferred embodiment, A' is nitrate, z is 0.01 to 0.2, $A^{n-}$ is $CO_3^{2-}$, and n=2.

The catalysts that are useful in the present invention are derived from a hydrotalcite of the formulas as defined above by a process comprising heating the hydrotalcite for a time and at a temperature sufficient to cause a diminution in the hydrotalcite powder X-ray diffraction pattern peak intensities between 2θ angles of 10 degrees and 70 degrees using CuKα radiation.

Catalysts derived from the hydrotalcite of Formula I can be synthesized by the following preferred method. A first aqueous solution containing M'A' is prepared. The solution can be prepared by adding ethylenediaminetetraacetic acid (EDTA) to water, adding hydroxide (preferably NaOH) until the EDTA is dissolved in the water, followed by adding an M' salt, preferably a nitrate, chloride or acetate salt. Most preferred are nitrate salts. Sodium, potassium or ammonium hydroxide is then added until a pH of about 10 is reached. The solution is then warmed to a temperature of about 60 to 70° C., preferably 65° C. Next, a second aqueous solution of $M^{2+}$ and $M^{3+}$ salts is prepared by dissolving the salts in water. The second solution containing the $M^{2+}$ and $M^{3+}$ salts is added drop-wise to the first solution. Alternatively, a plurality of individual metal salt solutions may be used, provided that they are added concurrently to the solution containing EDTA and the M' salt. The resulting suspension is warmed to a temperature of about 60 to 70° C., preferably 65° C. During the addition of the second solution to the first solution, the pH of the resulting suspension is monitored and adjusted, if necessary, to maintain a pH of about 10 using hydroxide (with soluble metal carbonate or bicarbonate if $A^{n-}$ is chosen to be $CO_3^{2-}$).

The resulting suspension (i.e., a precipitate suspended in a liquid) can be aged, preferably for approximately 18 hours, at 60 to 70° C. The precipitate is then separated, generally by filtering, and subsequently dried (generally in a vacuum oven or in air). The dried precipitate can be analyzed by powder X-ray diffraction to confirm the presence of a hydrotalcite phase. This phase is isostructural with the hydrotalcite $Mg_6Al_2(CO_3)(OH)_{16}.4H_2O$ (JCPDS card #54-1030; Powder Diffraction Files, International Centre for Diffraction Data, 1601 Park Lane, Swarthmore, Pa. 19081). The dried precipitate is then calcined by heating it for a time and at a temperature sufficient to cause a diminution in the hydrotalcite powder X-ray diffraction pattern peak intensities between 2θ angles of 10 degrees and 70 degrees using CuKα radiation. The calcined material can be analyzed by powder X-ray diffraction to confirm the diminution (including the complete absence) in these peak intensities and the appearance of new peaks corresponding to a material which is isostructural with partially crystalline magnesium oxide (MgO, JCPDS card #65-0476). Partial decomposition is preferably achieved by calcining the dried precipitate for a time and at a temperature sufficient to substantially reduce the peak intensities characteristic of the hydrotalcite phase.

Catalysts derived from the hydrotalcite of Formula II can be synthesized by the following method. An aqueous salt solution containing (a) magnesium and one or more divalent metals selected from the group consisting of nickel, cobalt and (b) aluminum and, optionally, one or more trivalent metals selected from the group consisting of iron and chromium is prepared. Preferred salts are nitrates, chlorides, or acetates. Most preferred are nitrates. The salt solution is added to a basic, aqueous solution containing sodium or potassium carbonate (or bicarbonate), sodium, potassium or ammonium hydroxide, or a mixture of the foregoing carbonates, bicarbonates and hydroxides, thereby providing the carbonate ion or hydroxide ion for $A^{n-}$, as well as the carbonate ion for A'. (Alternatively, a plurality of individual metal salt solutions may be used, provided that they are added concurrently to the basic, aqueous solution containing the carbonate, bicarbonate, hydroxide or mixtures thereof.) The pH of this basic solution is typically adjusted to a pH of approximately 10 during the addition of the aqueous salt solution. Preferably, the (a) magnesium and at least one other divalent metal and the (b) aluminum and optional trivalent metals should be in a molar ratio (a)/(b) between 0.5/1 and 9/1 inclusive (i.e., including the endpoints of the range).

The resulting suspension that is formed (i.e., a precipitate suspended in a liquid) can be aged, preferably for approxi- mately 18 hours, at 60° C. to 70° C. The precipitate is then separated, generally by filtering, and subsequently dried (generally in a vacuum oven or in air). The dried precipitate can be analyzed by powder X-ray diffraction to confirm the presence of a hydrotalcite phase. This phase is isostructural with the hydrotalcite $Mg_6Al_2(CO_3)(OH)_{16}.4H_2O$ (JCPDS card #54-1030; Powder Diffraction Files, International Centre for Diffraction Data, 1601 Park Lane, Swarthmore, Pa. 19081). The dried precipitate is then calcined by heating it for a time and at a temperature sufficient to cause a diminution in the hydrotalcite powder X-ray diffraction pattern peak intensities between 2θ angles of 10 degrees and 70 degrees using CuKα radiation. The calcined material can be analyzed by powder X-ray diffraction to confirm the diminution (including the complete absence) in these peak intensities and the appearance of new peaks corresponding to a material which is isostructural with partially crystalline magnesium oxide (MgO, JCPDS card #65-0476). Partial decomposition is preferably achieved by calcining the dried precipitate for a time and at a temperature sufficient to substantially reduce the peak intensities characteristic of the hydrotalcite phase.

For catalysts derived from hydrotalcites of Formula I and Formula II, although any calcination protocol can be used, one that is particularly useful on a laboratory scale includes heating the hydrotalcite in a one inch (2.5 cm) diameter tube furnace from 25 to 360° C. over 140 minutes at 2.4° C. per minute, and then holding at 360° C. for 2 to 4 hours.

Catalysts derived from the hydrotalcite of Formula III or Formula IV can be synthesized by the following method. An aqueous salt solution containing (a) magnesium and one or more divalent metals selected from the group consisting of zinc, nickel, palladium, platinum, cobalt, iron, and copper and (b) aluminum and, optionally, one or more trivalent metals selected from the group consisting of iron and chromium is prepared. Preferred salts are nitrates, chlorides, or acetates. Most preferred are nitrates. The salt solution is added to a basic, aqueous solution containing sodium or potassium carbonate (or bicarbonate), sodium, potassium or ammonium hydroxide, or a mixture of the foregoing carbonates, bicarbonates and hydroxides, thereby providing the carbonate ion or hydroxide ion for $A''^-$, as well as the carbonate ion for A'. The pH of this basic solution is typically adjusted to a pH of approximately 10 during the addition of the aqueous salt solution. The (a) magnesium and at least one other divalent metal and the (b) aluminum and optional trivalent metals should be in a molar ratio (a)/(b) between 0.5/1 and 9/1 inclusive (i.e., including the endpoints of the range) to satisfy the stoichiometry of the hydrotalcite component of the above formula. In practice, however, when M' is Ni or Co, the endpoints of the range should exceed 0.5/1 and 9/1 by an amount sufficient to satisfy the value of "z" for the [M'A'] component of the above formula. This is because, when M' is Ni or Co, the metal M' is selected from the same group of metals as the metals that can substitute for divalent magnesium in the hydrotalcite component of the formula. (Alternatively, a plurality of individual metal salt solutions may be used, provided that they are added concurrently to the basic, aqueous solution containing the carbonate, bicarbonate, hydroxide or mixtures thereof.)

The resulting suspension that is formed (i.e., a precipitate suspended in a liquid) can be aged, preferably for approximately 18 hours, at 60° C. to 70° C. The precipitate is then separated, generally by filtering, and subsequently dried (generally in a vacuum oven or in air). The dried precipitate can be analyzed by powder X-ray diffraction to confirm the presence of a hydrotalcite phase. This phase is isostructural with the hydrotalcite $Mg_6Al_2(CO_3)(OH)_{16}.4H_2O$ (JCPDS card #54-1030; Powder Diffraction Files, International Centre for Diffraction Data, 1601 Park Lane, Swarthmore, Pa. 19081). The dried precipitate is then calcined by heating it for a time and at a temperature sufficient to cause a diminution in the hydrotalcite powder X-ray diffraction pattern peak intensities between 2θ angles of 10 degrees and 70 degrees using CuKα radiation. The calcined material can be analyzed by powder X-ray diffraction to confirm the diminution (including the complete absence) in these peak intensities and the appearance of new peaks corresponding to a material which is isostructural with partially crystalline magnesium oxide (MgO, JCPDS card #65-0476). It is preferred to calcine the dried precipitate for a time and at a temperature sufficient to substantially reduce the peak intensities characteristic of the hydrotalcite phase.

A preformed hydrotalcite, of the following general formula can be used. A solution of nickel or cobalt nitrate can be contacted with the surface of the hydrotalcite so that nickel or cobalt nitrate is incorporated onto the surface of the hydrotalcite. For example, imbibing of the aqueous solution can be accomplished by incipient wetness, where the pore volume of the hydrotalcite is not exceeded by the volume of aqueous solution which is contacted with it. Multiple contacting and drying cycles can be used to achieve the proper stoichiometry of nickel or cobalt salt on the hydrotalcite, if necessary. Other methods of contacting the hydrotalcite with the aqueous solution can be used, which can involve spray coating the aqueous solution onto the preformed hydrotalcite, or immersing the hydrotalcite with excess solution followed by decantation.

After drying, the surface-impregnated hydrotalcite formed by any of these methods is then calcined by heating it for a time and at a temperature sufficient to cause a diminution in the hydrotalcite powder X-ray diffraction pattern peak intensities between 2θ angles of 10 degrees and 70 degrees using CuKα radiation. It is preferred to calcine the material for a time and at a temperature sufficient to substantially reduce the peak intensities characteristic of the hydrotalcite phase.

For catalysts derived from hydrotalcites of Formula III and Formula IV, although any calcination protocol can be used, one that is particularly useful on a laboratory scale includes heating the hydrotalcite in a one inch (2.5 cm) diameter tube furnace from about 25° C. to about 475° C. at 30° C. per minute, and then to 550° C. at 2° C. per minute, and then holding at 550° C. for about 8 hours.

The catalysts usable in the process of the invention can be prepared as described above. The catalysts may be used in the form of powders, granules, or other particulate forms. Selection of an optimal average particle size for the catalyst will depend upon such process parameters as reactor residence time and desired reactor flow rates.

In the process for making a reaction product comprising 1-butanol, a stream of gas phase ethanol containing water is contacted with at least one thermally decomposed hydrotalcite catalyst at a temperature and pressure sufficient to produce a reaction product comprising 1-butanol. The wet ethanol stream may be diluted with an inert gas, for example nitrogen, argon, carbon dioxide, or a combination of these. The ethanol can contain from about 0.5 weight percent to about 20 weight percent water, for example from about 2 weight percent water to about 8 weight percent water. Suitable temperatures are in the range of about 150° C. to about 500° C., for example about 200° C. to about 500° C. Suitable pressures are from about 0.1 MPa to about 20.7 MPa. The reaction product can further comprise water, unreacted etha nol (if less than complete ethanol conversion occurs), other butanol isomers, higher alcohols, and other organic species. The butanol is predominantly 1-butanol.

The catalysts useful in the process of the invention have been found to be surprisingly tolerant of water. This is indicated by their continued activity when a wet ethanol feed stream is used. Additionally, catalyst activity has been observed to improve with longer time on stream, which corresponds to longer exposure to the water generated during the conversion of ethanol to butanol. Applicants find convenient for catalyst activity comparisons a calculation termed the "Wet:Dry Activity Ratio," which is expressed as a percentage. The Wet:Dry Activity Ratio is a numerical value reflecting the relative conversions at a given time and comparing the activity of a catalyst with a wet ethanol feed and with a dry ethanol feed. To be meaningful, the determination of the ratio is made using the same catalyst under the same reaction conditions and for the same time on stream. As catalyst activity results are a function of time on stream, Wet:Dry Activity Ratios for longer time on stream data are more representative of a catalyst's water tolerance. A Wet:Dry Activity Ratio that is less than 100% means that the catalyst's activity is greater with dry ethanol feed than with wet ethanol feed for that amount of time on stream. A Wet:Dry Activity Ratio that is greater than 100% means that the catalyst's activity is greater with wet ethanol feed than with dry ethanol feed for that amount of time on stream. A Wet:Dry Activity Ratio that is about 100% means that the catalyst's activity is about the same with wet ethanol as for dry ethanol for that amount of time on stream.

Wet:Dry Activity Ratios are calculated from the Relative Conversion Test, which is described here. Catalyst is loaded on a stainless steel mesh support within a 18"×½" (45.7 cm×1.3 cm) outside diameter (o.d.) type 316 stainless steel tube reactor with inlets for gas and liquid feeds and preconditioned in situ as described in the Examples. After conditioning, the catalyst is evaluated at 300° C. using a nitrogen flow of 3 mL/min and a feed flow of 1.0 mL/hour. Anhydrous ethanol is fed to the reactor for approximately 350 minutes and the gaseous product stream is analyzed by GC approximately every 45 minutes. In a separate evaluation using a freshly conditioned catalyst, ethanol containing water (8 percent by weight in the Examples) is fed to the reactor for approximately 350 minutes and the gaseous product stream is analyzed by GC approximately every 45 minutes.

From the GC data, ethanol conversion is calculated for the anhydrous and wet ethanol feeds at selected times. Ethanol conversion (%) is calculated as follows: [(1−carbon moles of unreacted ethanol)/carbon moles of total outlet gases] multiplied by 100. To compare the relative activities of the catalyst with wet and dry ethanol feeds, the Wet:Dry Activity Ratio is calculated as follows: [(% ethanol conversion for the wet ethanol feed)/(% ethanol conversion for the dry ethanol feed)] multiplied by 100.

The catalytic conversion of ethanol to the reaction product comprising 1-butanol can be run in either batch or continuous mode as described, for example, in H. Scott Fogler, (*Elements of Chemical Reaction Engineering*, $2^{nd}$ Edition, (1992) Prentice-Hall Inc, CA). Suitable reactors include fixed-bed, adiabatic, fluid-bed, transport bed, and moving bed.

It is preferable, but not essential, to treat the catalyst, prior to its use, with nitrogen or air at elevated temperatures, which is thought to remove unwanted carbonates from the catalyst surface. If the starting hydrotalcite contains Ni, Pd, Pt, Co, or Cu, it is also preferred, but not essential, to treat the catalyst, prior to its use, with hydrogen at elevated temperatures. Protocols that has been found to be effective are described in more detail in the Examples, below. If catalyst treatment is desired, the catalyst may be treated in situ in the reactor or ex situ and then introduced into the reactor.

During the course of the reaction, the catalyst may become fouled, and therefore it may be necessary to regenerate the catalyst. Preferred methods of catalyst regeneration include, contacting the catalyst with a gas such as, but not limited to, air, steam, hydrogen, nitrogen or combinations thereof, at an elevated temperature, although care must be taken not to use a temperature that is so high that the regeneration results in a loss of surface area or other unwanted effects. If catalyst regeneration is desired, the catalyst may be regenerated in situ in the reactor or ex situ and then introduced into the reactor.

One skilled in the art will know that conditions, such as temperature, catalytic metal, catalyst support, reactor configuration and time can affect the reaction kinetics, product yield and product selectivity. Standard experimentation can be used to optimize the yield of 1-butanol from the reaction.

1-Butanol can be separated from the reaction product by known chemical engineering methods, including distillation. Other specific chemicals (or combinations of chemicals) also can be removed from the reaction product using known chemical engineering methods. The specific methods will be dependent on the nature of the reaction product, which, in turn, is dependent on the specific catalyst used and the reaction conditions, particularly the extent of ethanol conversion.

EXAMPLES

Ethanol was obtained from Sigma-Aldrich (St. Louis, Mo.). Pural® MG-70 hydrotalcite is commercially available from Sasol (Johannesburg, South Africa), calcium acetate is commercially available from EM Sciences (Gibbstown, N.J.), potassium acetate is commercially available from EM Sciences (Gibbstown, N.J.), ethylenediaminetetraacetic acid (EDTA) was obtained from Sigma-Aldrich (St. Louis, Mo.), nickel(II) nitrate hexahydrate was obtained from Sigma-Aldrich (St. Louis, Mo.), cobalt(II) nitrate hexahydrate was obtained from Alfa Aesar (Ward Hill, Mass.), 2M NaOH solution was obtained from J T Baker (Phillipsburg, N.J.), aluminum nitrate was obtained from EMD Sciences (Gibbstown, N.J.), and magnesium nitrate was obtained from EMD Sciences (Gibbstown, N.J.). Lanthanum-promoted γ-alumina catalyst support AL2301 was obtained from Davison Chemical. This material contains 4 weight percent $La_2O_3$ and 96 weight percent γ-$Al_2O_3$.

In the Examples, the catalysts were evaluated using the procedure of the Relative Conversion Test.

Example 1

$[M^{2+}_{1-x}M^{3+}_x(OH)_2][\{(M'A'\}_a A^{n-}_{(1-a)(n'/n)}]_{x/n'} \cdot yH_2O$
wherein
$M^{2+}$ is divalent Mg; $M^{3+}$ is trivalent Al; x=0.2; a=0.1; A' is the anion of ethylenediaminetetraacetic acid; M'=Ni; $A^{n-}$=$OH^-$; n'=2, n=1.

Catalyst Preparation:

11.09 g of ethylenediaminetetraacetic acid was dissolved in 250 mL of water in a three neck, round bottom flask and heated to 65° C. Enough sodium hydroxide (2M NaOH solution) was added to completely dissolve the EDTA. 1.028 g of nickel nitrate ($Ni(NO_3)_2 \cdot 6H_2O$) was then dissolved in the preheated solution containing the EDTA. Following the addition of nickel nitrate, the pH was adjusted to about 10 by adding 2M NaOH solution. Separate solutions of aluminum nitrate and magnesium nitrate were prepared as follows: 21.067 g of aluminum nitrate ($Al(NO_3)_3 \cdot 9H_2O$ was dissolved in 100 mL of water, and 57.6 g of magnesium nitrate (Mg (NO$_3$)$_2$.6H$_2$O was dissolved in 100 mL of water. The two solutions were added drop-wise and concurrently to the preheated solution containing EDTA and nickel. The time for this addition was about 45 minutes. During this addition, sodium hydroxide solution was added to maintain a pH of about 10. The preheated solution was stirred during the addition of the metal nitrates. After complete addition of these metal nitrates, the suspension was kept at 65° C. with stirring for 1 hr and then aged at this temperature for 18 hours without stirring. The precipitate was separated from solution by filtering. The synthesized separated solids were dried in vacuum oven at 90° C. for 48 hrs and calcined at 360° C. for 2 hours in nitrogen. The heating protocol was as follows: the precipitate was placed in a 1 inch diameter tube furnace, and the temperature was increased from 25 to 360° C. at 2.4° C. per minute over the course of 140 minutes, followed by 360° C. for 2 hours.

The calcined material was pelletized at 20,000 psig into small disks, granulated and sieved on −20, +40 mesh screens prior to reactor evaluations.

Reactor Evaluation:

Approximately 2 grams of catalyst was loaded on a stainless steel mesh support within an 18 inch×½ inch (45.7 cm×1.3 cm) outside diameter (o.d.) type 316 stainless steel tube reactor with inlets for gas and liquid feeds. The catalyst was then pre-conditioned in situ in the reactor by flowing nitrogen gas, initially at room temperature, raising the temperature to 180° C., flowing hydrogen gas at 15 cc/min for one hour, reintroducing nitrogen gas at a flow rate of 3 mL/min, and increasing the reactor temperature to 300° C., and introducing the ethanol or ethanol with 8 wt % water added to generate reaction data. At reaction temperature nitrogen flow was set at 3 mL/min and ethanol flow at 1.0 mL/hr. The gaseous product stream was kept at 215° C. and fed directly to an Agilent™ 6890 GC equipped with flame ionization and mass selective detectors. Results are shown in Table 1 below, wherein "EtOH" means ethanol, "Conv." means conversion, and "Sel." means selectivity. Ethanol conversion (%) was calculated as follows: [(1−carbon moles of unreacted ethanol)/carbon moles of total outlet gases] times 100. Total Alcohol

Selectivity (%) was calculated as follows: (carbon moles of product/carbon moles of ethanol reacted) times 100. Wet:Dry activity ratio shows the relative conversion at a set time comparing 8% water containing EtOH feed with anhydrous EtOH feed. Wet:Dry activity ratio is calculated as follows: [(% ethanol conversion for the wet ethanol feed)/(% ethanol conversion for the dry ethanol feed)] multiplied by 100.

TABLE 1

Results for the Catalyst of Example 1.

| Elapsed Time (min) | EtOH Conv. (8% water) | EtOH Conv. (Dry) | Total Alcohol Sel. 8% Water | Total Alcohol Sel. Dry | Wet:Dry Activity Ratio |
|---|---|---|---|---|---|
| 84 | 67.0 | 44.7 | 74.7 | 65.9 | 150% |
| 123 | 45.7 | 40.3 | 74.3 | 66.8 | 113% |
| 162 | 48.0 | 34.6 | 76.5 | 66.8 | 139% |

Figure 1:
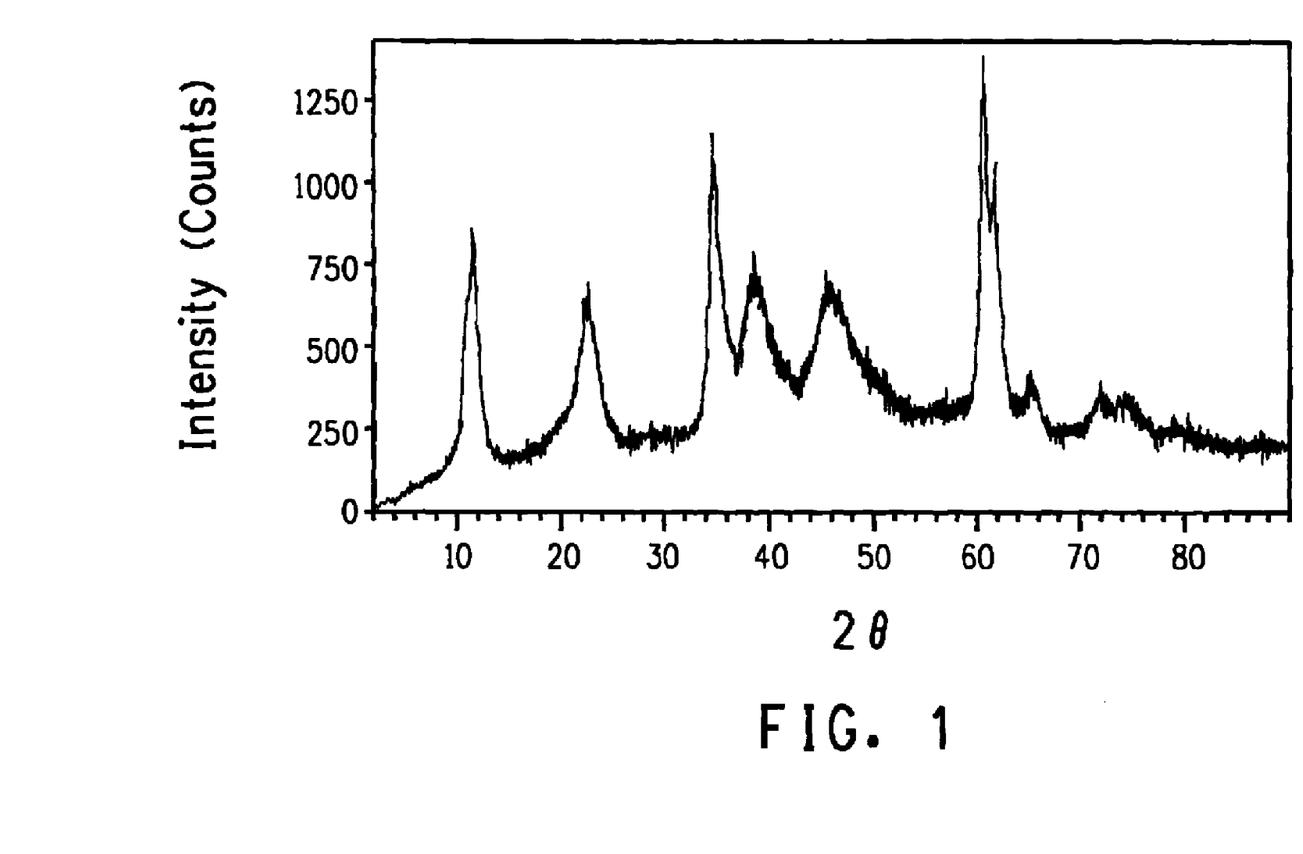
FIG. 1 shows the powder X-ray diffraction pattern of the hydrotalcite material of Example 2 before calcination, and indicates reflections typical of a hydrotalcite phase.
Figure 2:
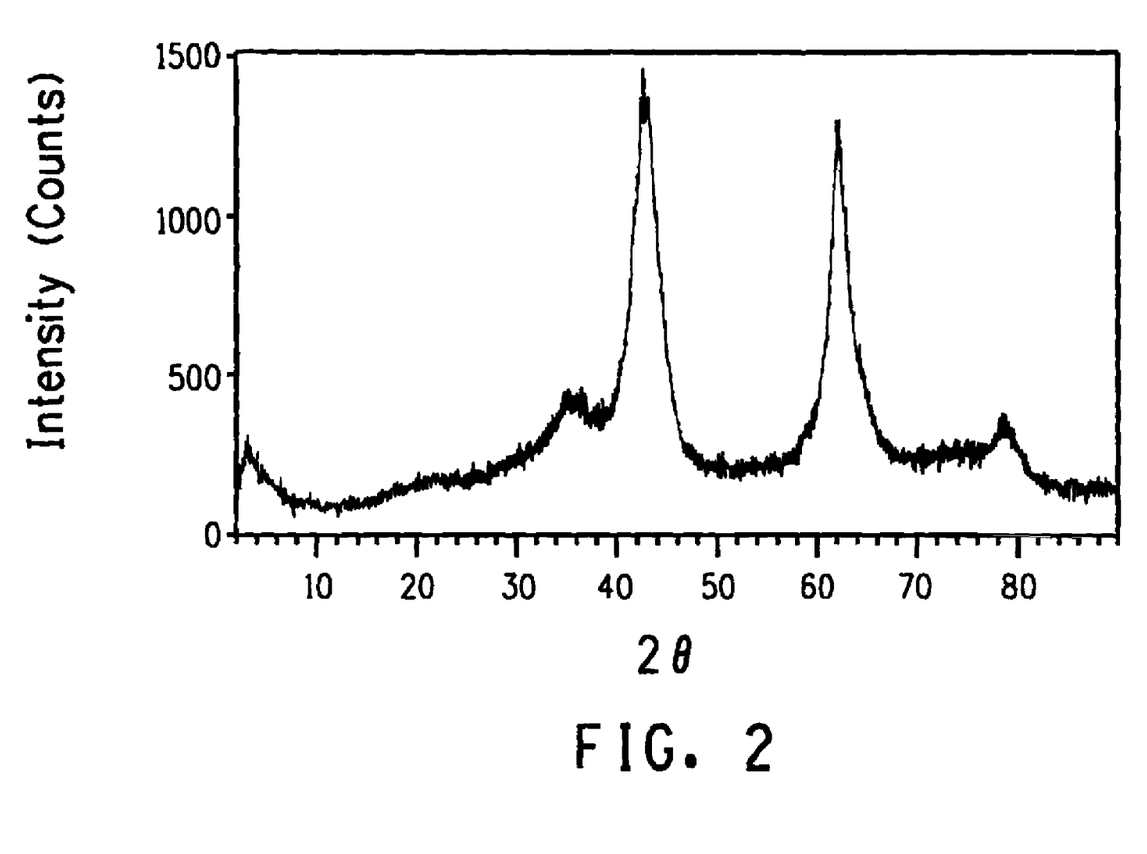
FIG. 2 shows a powder X-ray diffraction pattern of the material of Example 2 after calcination, showing decomposition of the hydrotalcite phase by the substantial loss of those reflections that are typical of a hydrotalcite phase.

Example 2 wherein
$M^{2+}$ is divalent Mg; $M^{3+}$ is trivalent Al; x=0.25; a=0.44; A' is the anion of ethylenediaminetetraacetic acid; M'=Co; $A''^-$=OH$^-$; n'=2, n=1.

Catalyst Preparation:

11.09 g of ethylenediaminetetraacetic acid was dissolved in 250 mL of water in a three neck, round bottom flask and heated to 65° C. Enough sodium hydroxide (2 M NaOH solution) was added to completely dissolve the EDTA. 4.8 g of cobalt nitrate Co(NO$_3$)$_2$.6H$_2$O was then dissolved in the preheated solution containing EDTA. Following the addition of cobalt nitrate, the pH was adjusted to about 10 by adding 2 M NaOH solution. Separate solutions of aluminum nitrate and magnesium nitrate were prepared as follows: 27.5 g of aluminum nitrate (Al(NO$_3$)$_3$.9H$_2$O and 57.6 g of magnesium nitrate (Mg(NO$_3$)$_2$.6H$_2$O were each dissolved in 100 mL of water, and the two solutions were added drop-wise (concurrently) to the preheated solution containing EDTA and cobalt. The time for this addition was about 45 minutes. During this addition, sodium hydroxide solution was added to maintain a pH of about 10. The preheated solution was stirred during the addition of the metal nitrates. After complete addition of these metal nitrates, the resulting suspension was kept at 65° C. with stirring for 1 hour (hr) and then aged at this temperature for 18 hours without stirring. The precipitate was separated from solution by filtering. The synthesized separated solids were dried in vacuum oven at 90° C. for 48 hrs and calcined at 360° C. for 2 hours in nitrogen. The heating protocol was as follows: the precipitate was placed in a 1 inch (2.5 cm) diameter tube furnace, and the temperature was increased from 25 to 360° C. at 2.4° C. per minute over the course of 140 minutes, followed by 360° C. for 2 hours.

Figure 3:
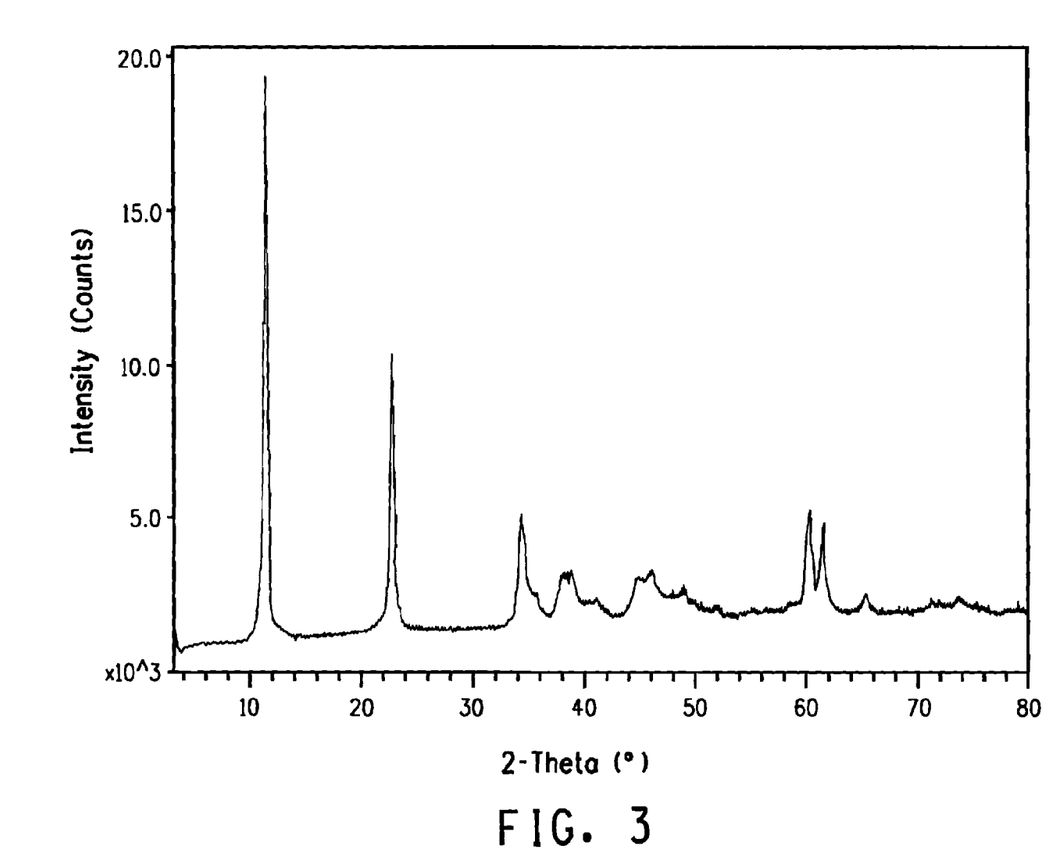
FIG. 3 shows the powder X-ray diffraction pattern of the hydrotalcite material of Example 3 before calcination, and indicates reflections typical of a hydrotalcite phase.
Figure 4:
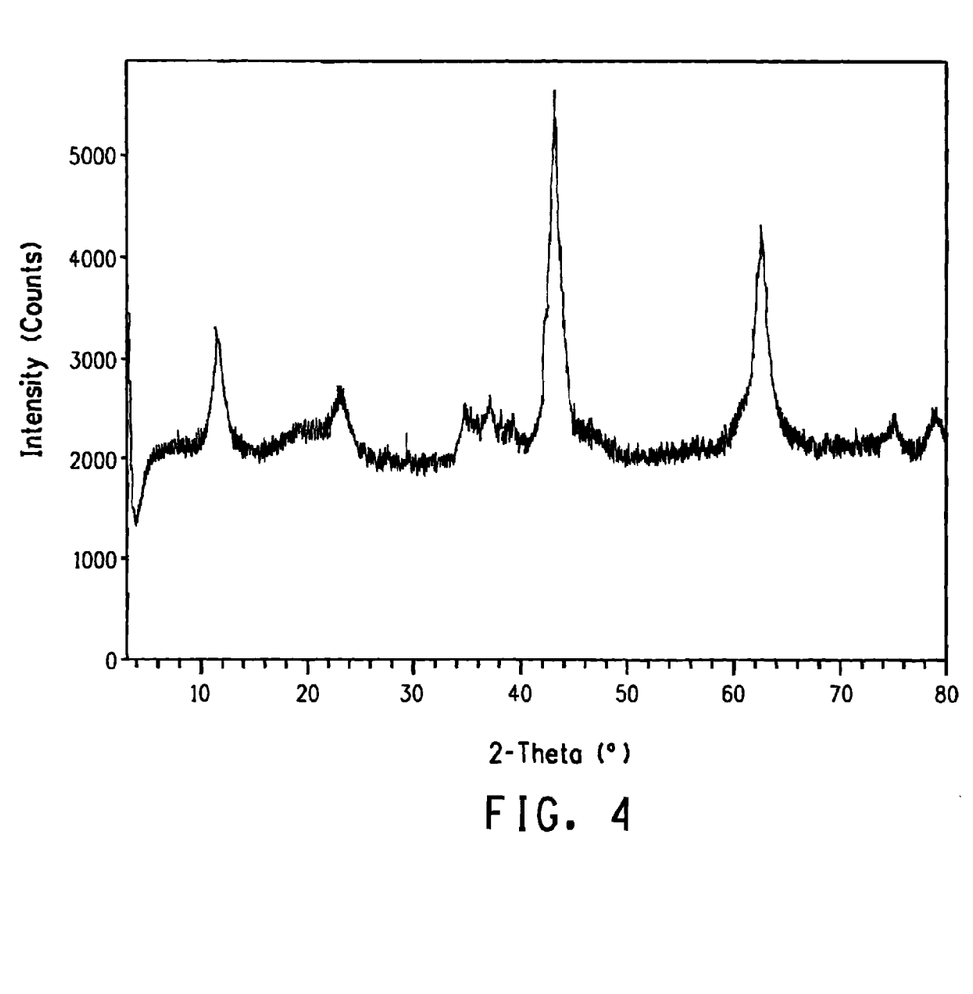
FIG. 4 shows a powder X-ray diffraction pattern of the material of Example 3 after calcination, showing decomposition of the hydrotalcite phase by the substantial loss of those reflections that are typical of a hydrotalcite phase.

Example 3 wherein
$M^{2+}$ is divalent Mg, $M^{3+}$ is trivalent Al; x=0.25; $A''^-$ is $CO_3^{2-}$; n=2; M' is Ni, A' is $NO_3^{2-}$; z=0.06; and y is 4.

Catalyst Preparation:

20.02 g MG-70 hydrotalcite (Sasol Pural MG-70 hydrotalcite, lot #D1086) was placed in a beaker. In a second beaker 4.57 g nickel(II) nitrate hexahydrate (Lot #04919AE) and 14.01 g deionized water were combined and stirred until the solids were dissolved. The contents were poured into the beaker containing the hydrotalcite powder with stirring to ensure uniform mixing. An additional 4.82 g of deionized water were added while stirring to take the powder to just beyond incipient wetness. The beaker was placed in a 70° C. vacuum oven overnight to dry. The dried solids were granulated by pressing at 20,000 psi for 30 seconds, and then screened to −20+40 mesh. 11.20 g of the granulated material was calcined in air by heating at 30° C./minute to 475° C., then at 2° C./minute from 475° C. to 550° C., and holding at 550° C. for 8 hours.

Reactor Evaluation:

Approximately 3 cc of catalyst was loaded on a stainless steel mesh support within a 18 inch×½ inch (45.7 cm×1.3 cm) outside diameter (o.d.) type 316 stainless steel tube reactor with inlets for gas and liquid feeds. The catalyst was then pre-conditioned in situ in the reactor by flowing nitrogen gas at 3 mL/min, initially at room temperature, raising the temperature to 300° C., and introducing the ethanol or ethanol with 8 wt % water added to generate reaction data. At reaction temperature nitrogen flow was set at 3 mL/min and ethanol flow at 1.0 mL/hr. The gaseous product stream was kept at 215° C. and fed directly to an Agilent™ 6890 GC equipped with flame ionization and mass selective detectors. Results are shown in Table 2 below, wherein "EtOH" means ethanol, "Conv." means conversion, and "Sel." means selectivity. Ethanol conversion (%) was calculated as follows: [(1−carbon moles of unreacted ethanol)/carbon moles of total outlet gases] multiplied by 100. Total Alcohol Selectivity (%) was calculated as follows: (carbon moles of product/carbon moles of ethanol reacted) multiplied by 100. Wet:Dry activity ratio shows the relative conversion at a set time comparing 8% water containing EtOH feed with anhydrous EtOH feed. Wet:Dry activity ratio is calculated as follows: [(% ethanol conversion for the wet ethanol feed)/(% ethanol conversion for the dry ethanol feed)] multiplied by 100.

TABLE 2

Results for the Catalyst of Example 3.

| Elapsed Time (min) | EtOH Conv. (8% water) | EtOH Conv. (Dry) | Total Alcohol Sel. 8% Water | Total Alcohol Sel. Dry | Wet:Dry Activity Ratio |
|---|---|---|---|---|---|
| 30 | 59.3 | 83.0 | 70.8 | 55.5 | 71% |
| 70 | 41.3 | 41.4 | 72.3 | 72.6 | 100% |
| 111 | 43.0 | 32.5 | 60.7 | 71.2 | 132% |
| 152 | 38.4 | 23.0 | 62.2 | 68.4 | 167% |
| 234 | 29.0 | 16.9 | 64.4 | 67.4 | 172% |

Comparative Example A $(M^{2+}_{1-x}M^{3+}_x(OH)_2)(A^{n-}_{x/n}) \cdot yH_2O$ wherein $M^{2+}$ is divalent Mg; $M^{3+}$ is trivalent Al; x is 0.25; $A^{n-}$ is $CO_3^{2-}$ with n=2; and y=0 to 4. This catalyst can also be formulated as $[[(M^{2+}_{1-x} M^{3+}_x(OH)_2)(A^{n-}_{x/n})] \cdot yH_2O][M'(A')_2]_z$ wherein $M^{2+}$ is divalent Mg; $M^{3+}$ is trivalent Al; x=0.25; $A^{n-}=CO_3^{2-}$; n=2; z=0 (material does not contain M' or A'). This is equivalent to the empirical formula $[Mg_6Al_2(OH)_{16}CO_3 \cdot yH_2O]$.
Catalyst Preparation:
  20.00 g MG-70 hydrotalcite (Sasol Pural MG-70 hydrotalcite, lot #D1086) were granulated by pressing at 20,000 psi for 30 seconds, and then screened to −20+40 mesh. 10.86 g of the granulated material was calcined in air by heating at 30° C./minute to 475° C., then at 2° C./minute from 475° C. to 550° C., and holding at 550° C. for 8 hours.
Reactor Evaluation:
  Approximately 3 cc of catalyst was loaded on a stainless steel mesh support within a 18 inch×½ inch (45.7 cm×1.3 cm) outside diameter (o.d.) type 316 stainless steel tube reactor with inlets for gas and liquid feeds. The catalyst was then pre-conditioned in situ in the reactor by flowing nitrogen gas, initially at room temperature, raising the temperature to 400° C., flowing air at 50 cc/min for one hour, reintroducing nitrogen gas at a flow rate of 3 mL/min, and decreasing the reactor temperature to 300° C., and introducing the ethanol or ethanol with 8 wt % water added to generate reaction data. At reaction temperature nitrogen flow was set at 3 mL/min and ethanol flow at 1.0 mL/hr. The gaseous product stream was kept at 215° C. and fed directly to an Agilent™ 6890 GC equipped with flame ionization and mass selective detectors. Results are shown in Table 3 below, wherein "EtOH" means ethanol, "Cony." means conversion, and "Sel." means selectivity. Ethanol conversion (%) was calculated as follows: [(1−carbon moles of unreacted ethanol)/carbon moles of total outlet gases] multiplied by 100. Total Alcohol Selectivity (%) was calculated as follows: (carbon moles of product/carbon moles of ethanol reacted) multiplied by 100. Wet:Dry activity ratio shows the relative conversion at a set time comparing 8% water containing EtOH feed with anhydrous EtOH feed. Wet:Dry activity ratio is calculated as follows: [(% ethanol conversion for the wet ethanol feed)/(% ethanol conversion for the dry ethanol feed)] multiplied by 100.

TABLE 3

Results for the Catalyst of Comparative Example A.

| Elapsed Time (min) | EtOH Conv. (8% water) | EtOH Conv. (Dry) | Total Alcohol Sel. 8% Water | Total Alcohol Sel. Dry | Wet:Dry Activity Ratio |
|---|---|---|---|---|---|
| 45 | 45.3 | 65.9 | 66.7 | 58.5 | 69% |
| 126 | 50.5 | 61.8 | 62.1 | 70.6 | 82% |
| 207 | 28.7 | 43.8 | 72.6 | 71.4 | 66% |
| 328 | 17.1 | 35.3 | 67.8 | 65.6 | 48% |

Comparative Example B 12.3 wt % CaO (Nominally as Calcium Oxide) Supported on Lanthanum-Stabilized Alumina Catalyst Preparation:
  8.809 g of calcium acetate was dissolved in 20 g of water. The liquid was slowly added to the support at near incipient wetness, adding the liquid in 20 mL aliquots (followed by overnight air drying) to 20 g of an alumina support (Davison, AL2301, Lot #204-QC50, lanthanum stabilized aluminum oxide).
  The material was calcined in a horizontal tube furnace according to the following protocol in flowing air (linear velocity of 20 cm/min): heat from 25-120° C. over 1.3 hours (1° C./min); hold at 120° C. for 4 hours; heat from 120° C. to 500° C. over 1.6 hours (3.8° C./min); soak at 500° C. for 6 hours; cool to room temperature. The calcined material was palletized at 20,000 psig into small disks, granulated and sieved on −20, +40 mesh screens prior to reactor evaluations.
Reactor Evaluation:
  Approximately 3 cc of the catalyst was loaded on a stainless steel mesh support within a 18 inch×½ inch (45.7 cm×1.3 cm) outside diameter (o.d.) type 316 stainless steel tube reactor with inlets for gas and liquid feeds. The catalyst was then pre-conditioned in situ in the reactor by flowing nitrogen gas, initially at room temperature, raising the temperature to 400° C., flowing air at 50 cc/min for one hour, reintroducing nitrogen gas at a flow rate of 3 mL/min, and decreasing the reactor temperature to 300° C., and introducing the ethanol or ethanol with 8 wt % water added to generate reaction data. At reaction temperature nitrogen flow was set at 3 mL/min and ethanol flow at 1.0 mL/hr. The gaseous product stream was kept at 215° C. and fed directly to an Agilent™ 6890 GC equipped with flame ionization and mass selective detectors. Results are shown in Table 4 below, wherein "EtOH" means ethanol, "Cony." means conversion, and "Sel." means selectivity. Ethanol conversion (%) was calculated as follows: [(1−carbon moles of unreacted ethanol)/carbon moles of total outlet gases] multiplied by 100. Total Alcohol Selectivity (%) was calculated as follows: (carbon moles of product/carbon moles of ethanol reacted) multiplied by 100. Wet:Dry activity ratio shows the relative conversion at a set time comparing 8% water containing EtOH feed with anhydrous EtOH feed. Wet:Dry activity ratio is calculated as follows: [(% ethanol conversion for the wet ethanol feed)/(% ethanol conversion for the dry ethanol feed)] multiplied by 100.

TABLE 4

Results for the Catalyst of Comparative Example B.

| Elapsed Time (min) | EtOH Conv. (8% water) | EtOH Conv. (Dry) | Total Alcohol Sel. 8% Water | Total Alcohol Sel. Dry | Wet:Dry Activity Ratio |
|---|---|---|---|---|---|
| 45 | 31.7 | 34.3 | 40.5 | 46.9 | 92% |
| 128 | 28.3 | 32.3 | 40.5 | 48.3 | 88% |
| 294 | 27.5 | 35.5 | 44.1 | 45.0 | 77% |

Comparative Example C 33.5 wt % $K_2O$ (Nominally as Potassium Oxide) Supported on Lanthanum-Stabilized Alumina Catalyst Preparation:

21.0 grams of g potassium acetate (EM Sciences, PX1330-1) was dissolved in 20 g of water. The liquid was slowly added to the support at near incipient wetness, adding the liquid in 20 mL aliquots (followed by overnight air drying) to 20 g of an alumina support, (Davison, AL2301, Lot #204-QC50, lanthanum stabilized aluminum oxide).

The material was calcined in a horizontal tube furnace according to the following protocol in flowing air (linear velocity of 20 cm/min): heat from 25-120° C. over 1.3 hours (1° C./min); soak at 120° C. for 4 hours; heat from 120° C. to 500° C. over 1.6 hours (3.8° C./min); soak at 500° C. for 6 hours; cool to room temperature. The calcined material was pelletized at 20,000 psig into small disks, granulated and sieved on −20, +40 mesh screens prior to reactor evaluations.

Reactor Evaluation:

Approximately 3 cc of the catalyst was loaded on a stainless steel mesh support within a 18 inch×½ inch (45.7 cm×1.3 cm) outside diameter (o.d.) type 316 stainless steel tube reactor with inlets for gas and liquid feeds. The catalyst was then pre-conditioned in situ in the reactor by flowing nitrogen gas, initially at room temperature, raising the temperature to 400° C., flowing air at 50 cc/min for one hour, reintroducing nitrogen gas at a flow rate of 3 mL/min, and decreasing the reactor temperature to 350° C., and introducing the ethanol or ethanol with 8 wt % water added to generate reaction data. At reaction temperature nitrogen flow was set at 3 mL/min and ethanol flow at 1.0 mL/hr. The gaseous product stream was kept at 215° C. and fed directly to an Agilent™ 6890 GC equipped with flame ionization and mass selective detectors. Results are shown in Table 5 below, wherein "EtOH" means ethanol, "Conv." means conversion, and "Sel." means selectivity. Ethanol conversion (%) was calculated as follows: [(1−carbon moles of unreacted ethanol)/carbon moles of total outlet gases] multiplied by 100. Total Alcohol Selectivity (%) was calculated as follows: (carbon moles of product/carbon moles of ethanol reacted) multiplied by 100. Wet:Dry activity ratio shows the relative conversion at a set time comparing 8% water containing EtOH feed with anhydrous EtOH feed. Wet:Dry activity ratio is calculated as follows: [(% ethanol conversion for the wet ethanol feed)/(% ethanol conversion for the dry ethanol feed)] multiplied by 100.

TABLE 5

Results for the Catalyst of Comparative Example C.

| Elapsed Time (min) | EtOH Conv. (8% water) | EtOH Conv. (Dry) | Total Alcohol Sel. 8% Water | Total Alcohol Sel. Dry | Wet:Dry Activity Ratio |
|---|---|---|---|---|---|
| 85 | 9.7 | 16.5 | 46.9 | 46.9 | 59% |
| 126 | 8.1 | 17.2 | 46.8 | 55.5 | 47% |
| 208 | 6.5 | 21.5 | 49.6 | 45.8 | 30% |
| 330 | 3.0 | 21.5 | 24.0 | 46.2 | 14% |

Although particular embodiments of the present invention have been described in the foregoing description, it will be understood by those skilled in the art that the invention is capable of numerous modifications, substitutions, and rearrangements without departing from the spirit or essential attributes of the invention. Reference should be made to the appended claims, rather than to the foregoing specification, as indicating the scope of the invention.

What is claimed is:

1. A process for making a reaction product comprising 1-butanol, comprising:
    contacting a reactant comprising ethanol containing water with a catalyst at a reaction temperature and pressure sufficient to produce said reaction product, wherein said catalyst is derived from a hydrotalcite of Formula I:

$$[M^{2+}{}_{1-x}M^{3+}{}_x(OH)_2][\{(M'A')^{n'-}\}_a A^{n-}{}_{(1-a)(n'/n)}]_{x/n} \cdot yH_2O \qquad \text{Formula I}$$

wherein $M^{2+}$ is divalent Mg, or a combination of divalent Mg and at least one divalent member selected from the group consisting of Zn, Ni, Pd, Pt, Co, Fe, and Cu;

$M^{3+}$ is trivalent Al, or a combination of trivalent Al and at least one trivalent member selected from the group consisting of Fe and Cr;

x is 0.66 to 0.1;

M' is one or more divalent members selected from the group consisting of Ni and Co;

A' is the anion of ethylenediaminetetraacetic acid;

n' is the absolute value of the sum of the oxidation state of M' and the oxidation state of the anion of ethylenediaminetetraacetic acid (−4);

$A^{n-}$ is $CO_3{}^{2-}$ with n=2 or $OH^-$ with n=1;

a=0.001 to 1; and y=0 to 4;

wherein the hydrotalcite catalyst is partially decomposed; and wherein the Wet:Dry Activity Ratio obtained by the Relative Conversion Test is greater than 100% after 70 minutes of time on stream.

2. A process for making a reaction product comprising 1-butanol, said process comprising:
    contacting a reactant comprising ethanol containing water with a catalyst at a reaction temperature and pressure sufficient to produce said product, wherein said catalyst is derived from a hydrotalcite of Formula II:

$$(M^{2+}{}_{1-x}M^{3+}{}_x(OH)_2)(A^{n-}{}_{x/n}) \cdot yH_2O \qquad \text{Formula II}$$

wherein $M^{2+}$ is divalent Mg and at least one divalent member selected from the group consisting of Ni and Co;

$M^{3+}$ is trivalent Al, or a combination of trivalent Al and at least one trivalent member selected from the group consisting of Fe and Cr;

x is 0.66 to 0.1;
$A^{n-}$ is $CO_3^{2-}$ with n=2 or $OH^-$ with n=1; and
y is 0 to 4;
wherein the hydrotalcite catalyst is partially decomposed;
and wherein the Wet:Dry Activity Ratio obtained by the Relative Conversion Test is greater than 100% after 70 minutes of time on stream.

3. A process for making a reaction product comprising 1-butanol, comprising:
contacting a reactant comprising ethanol containing water with a catalyst at a reaction temperature and pressure sufficient to produce the reaction product, wherein the catalyst is derived from a hydrotalcite of Formula III:

$$[[(Me^{2+}_{1-x}M^{3+}_x(OH)_2)(A^{n-}_{x/n})]\cdot yH_2O][M'A']_z \qquad \text{Formula III}$$

wherein
$M^{2+}$ is divalent Mg, or a combination of Mg and at least one divalent member selected from the group consisting of Zn, Ni, Pd, Pt, Co, Fe, and Cu;
$M^{3+}$ is trivalent Al, or a combination of trivalent Al and at least one trivalent member selected from the group consisting of Fe and Cr;
x is 0.66 to 0.1;
$A^{n-}$ is $CO_3^{2-}$ with n=2, or $OH^-$ with n=1;
M'A' is a carbonate of at least one divalent metal M' selected from the group consisting of Ni and Co; and A' is carbonate;
z is any number between 0.001 and 0.5 inclusive; and
y is 0 to 4;
wherein the hydrotalcite catalyst is partially decomposed;
and wherein the Wet:Dry Activity Ratio obtained by the Relative Conversion Test is greater than 100% after 70 minutes of time on stream.

4. A process for making a reaction product comprising 1-butanol, comprising:
contacting a reactant comprising ethanol containing water with a catalyst at a reaction temperature and pressure sufficient to produce the reaction product, wherein the catalyst is derived from a hydrotalcite of Formula IV:

$$[[(M^{2+}_{1-x}M^{3+}_x(OH)_2)(A^{n-}_{x/n})]\cdot yH_2O][M'(A')_2]_z \qquad \text{Formula IV}$$

wherein
$M^{2+}$ is divalent Mg, or a combination of Mg and at least one divalent member selected from the group consisting of Zn, Ni, Pd, Pt, Co, Fe, and Cu;
$M^{3+}$ is trivalent Al, or a combination of trivalent Al and at least one trivalent member selected from the group consisting of Fe and Cr;
x is 0.66 to 0.1;
$A^{n-}$ is $CO_3^{2-}$ with n=2, or $OH^-$ with n=1;
$M'(A')_2$ is a nitrate or hydroxide of at least one divalent metal M' selected from the group consisting of Ni and Co; and A' is nitrate or hydroxide;
z is any number between 0.001 and 0.5 inclusive;
y is 0 to 4;
wherein the hydrotalcite catalyst is partially decomposed;
and wherein the Wet:Dry Activity Ratio obtained by the Relative Conversion Test is greater than 100% after 70 minutes of time on stream.

5. The process of claim 1, 2, 3, or 4 wherein the hydrotalcite decomposition is achieved by heating for a time and at a temperature sufficient to cause a diminution in the hydrotalcite powder X-ray diffraction pattern peak intensities between 2θ angles of 10 degrees and 70 degrees using CuKα radiation.

6. The process of claim 1, 2, 3, or 4 wherein the ethanol contains about 0.5 weight percent to about 20 weight percent water.

7. The process of claim 1, 2, 3, or 4 wherein the reaction temperature is from about 200° C. to about 500° C. and the pressure is from about 0.1 MPa to about 20.7 MPa.

8. The process of claim 1, 2, 3, or 4 wherein the Wet:Dry Activity Ratio is greater than 100% after 90 minutes of time on stream.

9. The process of claim 1, 3, or 4 wherein $M^{2+}$ is divalent Mg.

10. The process of claim 1, 2, 3, or 4 wherein $M^{3+}$ is trivalent Al.

11. The process of claim 1, 2, 3, or 4 wherein $A^{n-}$ is $CO_3^{2-}$ or $OH^-$.

12. The process of claim 1, wherein $M^{2+}$ is divalent Mg; $M^{3+}$ is trivalent Al; x is 0.2; a is 0.1; A' is the anion of ethylenediaminetetraacetic acid; M' is Ni; $A^{n-}$ is $OH^-$; n' is 2; n is 1; and y is 0 to 4.

13. The process of claim 2, wherein $M^{2+}$ is divalent Mg and at least one divalent member selected from the group consisting of Ni and Co; $M^{3+}$ is trivalent Al: and $A^{n-}$ is $CO_3^{2-}$ or $OH^-$.

14. The process of claim 2, wherein $M^{2+}$ is divalent Mg and at least one divalent member selected from the group consisting of Ni and Co, and x is 0.35 to 0.1.

15. The process of claim 3, wherein $M^{2+}$ is divalent Mg; $M^{3+}$ is trivalent Al; $A^{n-}$ is $CO_3^{2-}$ or OH; z is any number between 0.001 and 0.5; and M' is selected from the group consisting of Ni and Co.

16. The process of claim 15, wherein z is any number between 0.01 and 0.25.

17. The process of claim 4, wherein $M^{2+}$ is divalent Mg; $M^{3+}$ is trivalent Al; x=0.25; $A^{n-}$ is $CO_3^{2-}$; M' is Ni; A' is nitrate; and z=0.06; and y is 0 to 4.

* * * * *

UNITED STATES PATENT AND TRADEMARK OFFICE
Certificate

Patent No. 8,318,989 B2                                          Patented: November 27, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Kostantinos Kourtakis, Media, PA (US); Ronnie Ozer, Arden (DE); Michael B. D'Amore, Wilmington, DE (US); and David R. Corbin, West Chester, PA (US).

Signed and Sealed this Seventh Day of January 2014.

<div align="right">
JOHANN R. RICHTER<br>
Supervisory Patent Examiner<br>
Art Unit 1621<br>
Technology Center 1600
</div>